United States Patent
Gamba

(10) Patent No.: US 11,858,903 B2
(45) Date of Patent: Jan. 2, 2024

(54) PROCESS FOR QUENCHING OFFGAS OF MELAMINE SYNTHESIS

(71) Applicant: Casale SA, Lugano (CH)

(72) Inventor: Simone Gamba, Pagazzano (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 17/912,445

(22) PCT Filed: Mar. 2, 2021

(86) PCT No.: PCT/EP2021/055130
§ 371 (c)(1),
(2) Date: Sep. 16, 2022

(87) PCT Pub. No.: WO2021/185564
PCT Pub. Date: Sep. 23, 2021

(65) Prior Publication Data
US 2023/0125818 A1 Apr. 27, 2023

(30) Foreign Application Priority Data
Mar. 18, 2020 (EP) ..................................... 20163999

(51) Int. Cl.
*C07D 251/60* (2006.01)
(52) U.S. Cl.
CPC .................................. *C07D 251/60* (2013.01)

(58) Field of Classification Search
CPC .................................................... C07D 251/60
See application file for complete search history.

(56) References Cited

U.S. PATENT DOCUMENTS 3,547,919 A 12/1970 Hamprecht

FOREIGN PATENT DOCUMENTS

| CN | 109415328 A | 3/2019 |
| DE | 102005023042 A1 | 11/2006 |
| WO | 03/080584 A1 | 10/2003 |

OTHER PUBLICATIONS

International Search Report dated Apr. 15, 2021 issued in connection with PCT/EP2021/055130.
Written Opinion of the International Searching Authority dated Apr. 15, 2021 issued in connection with PCT/EP2021/055130.
International Preliminary Report on Patentability dated Mar. 14, 2022 issued in connection with PCT/EP2021/055130.

*Primary Examiner* — Deepak R Rao
(74) *Attorney, Agent, or Firm* — Akerman LLP

(57) ABSTRACT

A process for the synthesis of melamine from urea, preferably of the high-pressure type, wherein offgas quenching is performed in a quenching vessel wherein in the upper part of the vessel, a rising flow of offgas is contacted in counter-current with liquid ammonia to obtain precipitation of melamine contained in the offgas and melamine-free anhydrous washed offgas; in the lower part of the vessel, the solid melamine is contacted with a liquid solvent to form a solution of melamine or a melamine slurry.

24 Claims, 1 Drawing Sheet

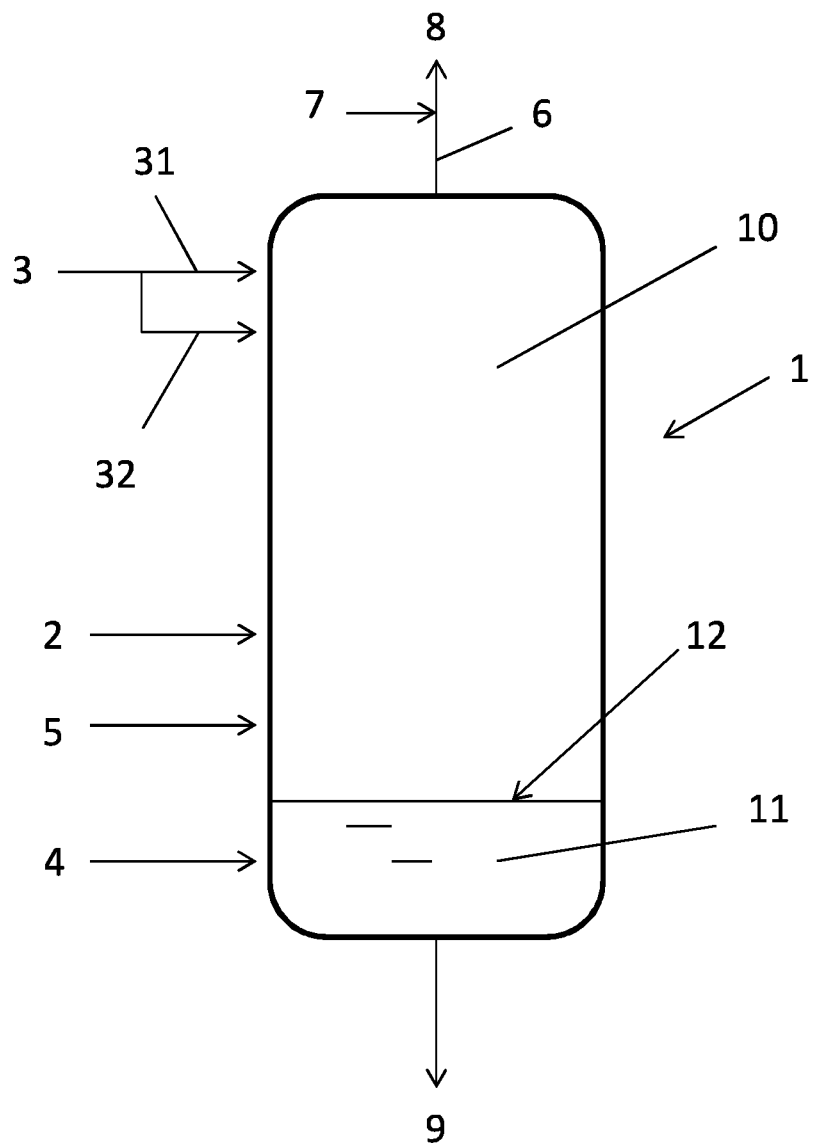

PROCESS FOR QUENCHING OFFGAS OF MELAMINE SYNTHESIS

CROSS-REFERENCE TO RELATED APPLICATIONS

This application is a national phase of PCT/EP2021/055130, filed Mar. 2, 2021, and claims priority to EP 20163999.4, filed Mar. 18, 2020, the entire contents of both of which are hereby incorporated by reference.

FIELD OF APPLICATION

The invention relates the field of synthesis of melamine from urea. The invention relates in particular to a process and equipment for quenching and scrubbing the ammonia and carbon dioxide-containing offgas generated during the synthesis of melamine.

PRIOR ART

The industrial synthesis of melamine from urea can be performed with the low-pressure gas-phase catalytic processes or the high-pressure liquid-phase non-catalytic process. Both are known in the art and widely described in the literature. They are normally referred to simply as "low-pressure" and "high-pressure".

In all processes for the synthesis of melamine, offgas predominantly composed of ammonia and carbon dioxide is generated. The offgas is typically recycled to a tied-in urea plant. Recycling the offgas to a urea plant is particularly attractive when the melamine is produced with the non-catalytic high-pressure liquid phase process because the offgas is made available at a high or medium pressure. However the offgas also contains some melamine which must be removed to make the offgas suitable for its recycle to a tied-in urea plant and to avoid losses of produced melamine.

A technique for removing melamine from offgas is washing/quenching with a suitable quenching medium, so that the melamine contained in the offgas cools down and precipitates in a solid form.

The known techniques for offgas washing, particularly to wash the offgas liberated by a high-pressure melamine process, include washing with urea melt and washing with water or an aqueous medium. The aqueous washing can be performed for example with an offgas washing column from which a water-saturated washed offgas stream and a melamine solution containing melamine, $CO_2$ and ammonia are obtained.

The urea melt washing may be preferred particularly in integrated urea-melamine plants. A water-based washing process may require a less expensive equipment in terms of resistance to corrosion, but has a disadvantage in that washed offgas are saturated with water, which is not desirable e.g. in view of their recycle to a tied-in urea plant. A second disadvantage of aqueous washing is that the melamine solution contains a significant amount of $CO_2$ and requires a stripping stage to remove $CO_2$.

WO 03/080584 discloses a process for the production of melamine from urea and for the separation of melamine from off-gas involving de-sublimation of melamine and formation of a gas-solid mixture in a mixer, with the help of a cooling fluid such as ammonia, and subsequent separation of the solid portion in a separator such as a cyclone followed by a filter.

SUMMARY OF THE INVENTION

The invention is aimed to a process and equipment for washing offgas in a melamine plant, obtaining a stream of substantially melamine-free anhydrous washed offgas and a melamine solution or suspension free or substantially free of dissolved ammonium carbonate or carbamate.

This aim is reached with a process according to the claims.

The process of the invention involves basically the following two steps.

In a first portion of a quenching vessel, an upward rising flow of the melamine-containing offgas is contacted in countercurrent with a descending flow of liquid ammonia. This step results in precipitation of solid melamine and formation of washed offgas with a reduced content of melamine or substantially melamine-free, which are withdrawn from said first portion of the vessel, for example from the top of the vessel.

In a second portion of said vessel, which is below said first portion, the precipitated solid melamine is contacted with a liquid solvent forming a solution of melamine or a melamine slurry, which is removed from the vessel.

The first portion of the vessel may be a top portion and the second portion of the vessel may be a bottom portion. The washed offgas may be withdrawn from top of the vessel and the solution or slurry may be removed from bottom of the vessel.

The liquid ammonia introduced in the vessel is colder than the melamine-containing input gas. The vessel can be termed offgas quencher or offgas scrubber because the offgas are quenched and scrubbed with the liquid ammonia.

The invention provides a two-zone quenching process. In an upper zone, which is for example in the upper part of the quencher, liquid ammonia is sprayed in order to cool down the offgas and solidify the melamine contained therein. Ammonia vaporizes in contact with the offgas stream and is removed together with washed offgas. In a lower zone, which is for example in the bottom part of the quencher, a suitable liquid solvent, e.g. water or an aqueous solvent, is introduced in order to remove the solidified melamine as an aqueous solution or slurry from the quencher bottom. Optionally, a suitable inert gas may also be introduced to form a separation layer between the liquid phase and the gaseous phase.

The main advantages of the invention are the following.

First, the washed offgas stream is anhydrous. This is a considerable advantage over water-based systems particularly in an integrated urea-melamine process because it reduces the introduction of water into the urea synthesis section. This advantage is of particular interest when the melamine process is of the high-pressure type. The ammonia used for the offgas washing is recovered in the washed offgas itself and can be recovered in a tied-in urea plant for urea production.

Second, the melamine solution or suspension obtained at the bottom of the scrubber is free or substantially free of ammonia and $CO_2$ being thus processable in both ammonia-based purification processes and metal-alkali based processes without the need of a dedicated offgas stripping stage.

An aspect of the invention is also a melamine plant according to the claims. Particularly preferably, the invention is applied to integrated urea and melamine synthesis, wherein the washed offgas are sent to a urea plant to recycle the ammonia and carbon dioxide contained therein for the synthesis of melamine.

The invention may be applied to catalytic low-pressure and non-catalytic high pressure melamine plants. Application to high-pressure melamine plants is particularly preferred.

PREFERRED EMBODIMENTS

In the quencher, the descending flow of liquid ammonia may be generated with one or more sprays of liquid ammonia. Ammonia is sprayed above the inlet of the offgas to be processed, in order to obtain a counter-current flow in the quencher. The quencher may be provided with one ammonia sprayer or a suitable set of ammonia sprayer. For example the quencher may be a cylindrical vessel and ammonia sprayers may be distributed around the diameter of the vessel at a suitable elevation above an inlet of the offgas to be processed.

A certain amount of the melamine-containing liquid or slurry may be collected at the bottom of the quencher and fill its bottom portion. Accordingly, a surface level is defined in the quencher. The liquid solvent is preferably introduced in the vessel below said surface level.

Preferably, injection of the liquid solvent in the lower part of the quencher is performed below the liquid level of the melamine solution or slurry and with a tangential inlet. A tangential inlet is preferred in order to minimize mixing at the vapor-liquid interface and to lower as much as possible the gas diffusion in the bulk of the liquid. Preferably the liquid injection is made in order to avoid creating turbulence at the gas/liquid interface to minimize the gas diffusion in the liquid phase.

In preferred embodiments, said liquid solvent is water or is predominantly composed of water. Particularly preferably said liquid solvent is demineralized water. In another preferred embodiment, said liquid solvent is recycled water taken from the melamine synthesis process.

A preferred embodiment includes also the introduction of an inert gas above said surface level defined by the melamine-containing solution or slurry. Said inert gas having a density greater than the density washed offgas, so that the inert gas forms a layer above the surface level of the solution or slurry. Preferably the inert gas is colder than the washed offgas. Preferably said inert gas is nitrogen.

An advantage of said introduction of inert gas is the formation of a cushion of inert gas between the melamine-containing liquid phase and the gaseous phase, which acts as a separation layer between the phases and prevents dissolution of ammonia and carbon dioxide in the liquid phase.

The pressure and temperature of the quenching process may be selected in order to avoid formation of deposits of ammonium carbonate/carbamate from the offgas.

The liquid solvent (e.g. water) is preferably introduced in the quencher at a temperature lower than the equilibrium temperature of the solvent at the quenching pressure (i.e., pressure at which the quenching process is performed). More preferably the liquid solvent is introduced at a temperature lower than the temperature of the washed offgas.

The temperature of the washed offgas is preferably lower than the equilibrium temperature of the liquid solvent at the quenching pressure. Preferably, the temperature of the washed offgas is equal to or greater than the critical temperature of ammonia (132.4° C.) and more preferably not greater than 260° C.

The residence time of the melamine solution or slurry in the bottom part of the quencher is preferably not greater than 10 min and particularly preferably not greater than 5 min. A low residence time is preferred for two reasons: (1) avoiding the saturation of the liquid phase with ammonia and/or carbon dioxide and avoiding the equalization of temperature between the offgas and the liquid; (2) minimizing the hydrolysis of melamine.

The process may include addition of $CO_2$ to the washed offgas. Addition of $CO_2$ is particularly preferred if recycle of the offgas in a tied-in urea plant involves the condensation of the offgas (e.g., in an offgas condensation section) and recycle of the so obtained condensate. In that case, the added $CO_2$ may to help the offgas condensation.

The process may include addition of ammonia to the solution or slurry, if appropriate. Particularly, addition of ammonia is provided if purification of the solution or slurry is performed with an ammonia-based purification process. Said purification may include filtration and crystallization of melamine. Addition of ammonia may be provided directly in the offgas quencher or, more preferably, downstream the offgas quencher.

In a melamine plant, an offgas quencher adapted to perform the process of the invention may comprise:
an offgas inlet;
at least one sprayer of liquid ammonia, which is above the offgas inlet;
an inlet for a liquid solvent, located in a bottom portion of the quencher below the offgas inlet;
an outlet for withdrawing washed offgas, which is located in the upper part and preferably on top of the quencher;
an outlet for a solution or slurry containing melamine removed from the offgas, which is located at the bottom of the quencher.

The sprayer of ammonia may be a single sprayer or a set of sprayers. In case of a plurality of sprayers, all sprayers are above the inlet of the offgas.

The quencher may also comprise an inlet for an inert gas, which is located above the inlet of the solvent and below the offgas inlet.

The terms of inlet and outlet may denote a single inlet or a plurality of inlets according to different embodiments.

The quencher is normally a cylindrical pressure vessel with a suitable top cover and bottom. The lower part of the quencher may have a smaller diameter than the upper part in order to minimize the vapor-liquid interface. The quencher may include a conical part between a larger portion and a smaller bottom portion with reduced diameter. In an embodiment, water nozzles may be provided to wash the conical part from possible deposits of melamine.

The invention is now further elucidated with the help of the drawings.

DESCRIPTION OF FIGURES

FIG. 1 is a sketch of a melamine offgas quencher according to a preferred embodiment of the invention.

DETAILED DESCRIPTION

FIG. 1 illustrates a melamine offgas quencher 1 which receives:
melamine-containing offgas via line 2;
liquid ammonia via line 3;
an aqueous solvent via line 4;
cold gaseous nitrogen via line 5.

The melamine-containing offgas in line 2 come from the synthesis section of a melamine plant, e.g. a non-catalytic high-pressure melamine synthesis section.

The liquid ammonia may be introduced via one or more sprays. For example the lines 31 and 32 in FIG. 1 denote different ammonia sprayers fed by the main header 3.

The aqueous solvent of line 4 may be demineralized water or recycled water or recycled mother liquor from the melamine plant. It may contain traces of ammonia and/or $CO_2$.

The cold gaseous nitrogen 5, which is an optional, is colder and therefore denser than the washed offgas.

As illustrated, liquid ammonia is introduced above the inlet of the offgas. The cold nitrogen of line 5 is introduced below the offgas inlet and the aqueous solvent is introduced below the nitrogen inlet at the bottom of the quencher 1.

Due to the location of the introduction points of the above described streams, the quencher 1 operates basically as a two-zone equipment.

The upper zone 10 operates in a gaseous phase. The offgas entering at line 2 travel upward and contact the liquid ammonia sprayed at lines 31, 32 in a counter-current regime. As a consequence of this, the melamine contained in the offgas is solidified and precipitates; melamine-free anhydrous offgas are extracted from top of the quencher 1 at line 6.

Optionally, the washed offgas are mixed with a $CO_2$ stream 7. The resulting stream 8 is sent to a tied-in urea plant for recycle, e.g. via offgas condensation and recycle of the so obtained carbamate-containing solution.

The lower zone 11 operates in a liquid phase. The solid melamine removed from the offgas is dissolved in the aqueous medium and partially fills the bottom of the quencher 1 forming a liquid level 12. As illustrated, in operation the input line 4 of the aqueous solvent remains preferably below the liquid level 12, whilst the nitrogen line 5 is above the liquid level 12. The melamine-containing solution is removed via line 9 for further processing.

The cold nitrogen, due to its density, tends to form a layer just above the liquid level 12, which separates the zones 10 and 11, particularly to avoid that gaseous $CO_2$ passes into the liquid phase.

In some embodiments, the lower portion of the quencher 1 (substantially corresponding to the zone 11) may be of a reduced diameter.

This melamine solution at line 9 can be sent to a downstream equipment for further purification. Before purification, the melamine solution withdrawn for the quencher 1 may be mixed with a melamine solution obtained from a step of melamine melt quenching, or the solution at line 9 may be sent directly to a step of filtration/crystallization but without the need of a dedicated offgas stripping stage.

Example 1

Reference is made to a high-pressure melamine plant with a capacity of 40000 tons/year wherein the offgas are released from the melamine synthesis section at 380° C. and 80 barg (bar gauge). A total of 13.0 tons/hour (t/h) of offgas are released, including 6.6 t/h of $NH_3$, 5.9 t/h of $CO_2$ and 0.5 t/h of melamine.

Said offgas is washed with ammonia introduced in liquid state at 20° C. and 80 barg. The offgas is cooled down to 169° C. The operating pressure of the quencher is 25 barg. The ammonia required for cooling down the offgas is 3.3 t/h.

The offgas obtained from the quencher at 169° C. and 25 barg is free of melamine and contains 9.9 t/h of ammonia and 5.9 t/h of $CO_2$.

At the bottom of the quencher, 4.5 t/h of water or water recycling solution at 140° C. are fed in order to obtain 5 t/h of a melamine solution containing 10% by weight of melamine. The solution is free or substantially free of dissolved offgas.

Example 2

This invention can be carried out even in a more advantageous embodiment by increasing the temperature of the washed offgas considering that the need of keeping a low-enough temperature in the offgas quencher (in order to minimize the water content in the washed offgas) is set aside. Increasing the washed offgas temperature decreases the amount of required quenching ammonia.

The offgas stream of example 1 is washed with ammonia in liquid state at 20° C. and 80 barg and cooled to 250° C. The operating pressure of the quencher is 40 barg. The ammonia required for cooling down the offgas is 2.0 t/h.

The offgas obtained from the quencher at 250° C. and 40 barg is free of melamine and contains 8.6 t/h of ammonia and 5.9 t/h of $CO_2$. At the bottom of the quencher, 2.2 t/h of water or water recycling solution at 170° C. are fed in order to obtain 2.7 t/h of a solution containing 18.5% by weight of melamine, which is free or substantially free of dissolved offgas.

What is claimed is:

1. A process for the synthesis of melamine from urea, wherein offgas containing ammonia, carbon dioxide and melamine, which are formed during the synthesis of melamine, are quenched to recover the melamine contained therein,
    wherein the quenching of the offgas comprises:
    in a first portion of a quenching vessel, contacting an upward rising flow of said offgas in countercurrent with a descending flow of liquid ammonia, resulting in precipitation of solid melamine and formation of washed offgas with a reduced content of melamine or substantially melamine-free, which are withdrawn from said first portion of the vessel;
    in a second portion of said vessel, which is below said first portion, contacting the precipitated solid melamine with a liquid solvent forming a solution of melamine or a melamine slurry, which is removed from the vessel.

2. The process according to claim 1, wherein the descending flow of liquid ammonia is generated with one or more sprays of liquid ammonia.

3. The process according to claim 1, wherein said solution or slurry is collected at the bottom of the vessel and fills a bottom portion of the vessel below a surface level.

4. The process according to claim 3, wherein said liquid solvent is introduced in the vessel below said surface level.

5. The process according to claim 3, further including the introduction of an inert gas above said surface level, said inert gas having a density greater than the washed offgas, so that a layer of inert gas is collected above the surface level of the solution or slurry.

6. The process according to claim 5, wherein said inert gas is nitrogen.

7. The process according to claim 1, wherein quenching is performed at a quenching pressure and said liquid solvent is introduced in the vessel at a temperature lower than the equilibrium temperature of the solvent at said quenching pressure.

8. The process according to claim 1, wherein the temperature of the washed offgas is lower than the equilibrium temperature of the liquid solvent at the quenching pressure.

9. The process according to claim 1, wherein the temperature of the washed offgas is equal to or greater than the critical temperature of ammonia.

10. The process according to claim 1, wherein the residence time of the melamine solution or slurry in the bottom part of the quencher is not greater than 10 min.

11. The process according to claim 1, wherein said solvent is an aqueous solvent, which is water or is predominantly composed of water.

12. The process according to claim 1, wherein the washed offgas are anhydrous.

13. The process according to claim 1, further including addition of CO2 to the washed offgas withdrawn from the quenching vessel.

14. The process according to claim 1, further including addition of ammonia to the melamine-containing liquid solution or slurry, which is performed directly in the quenching vessel or downstream the vessel.

15. The process according to claim 1, wherein washed offgas are sent to a tied-in urea plant to provide an input of ammonia and carbon dioxide for the synthesis of urea.

16. A melamine plant, comprising a melamine synthesis reactor where urea is converted to melamine with formation of offgas containing ammonia, carbon dioxide and melamine, and a quencher where said offgas are quenched to recover melamine contained therein, wherein said quencher comprises:
   an offgas inlet;
   at least one sprayer of liquid ammonia, which is above the offgas inlet;
   an inlet for a liquid solvent located in a bottom portion of the quencher below the offgas inlet;
   an outlet for withdrawing washed offgas, which is located in the upper part of the quencher;
   an outlet for a solution or slurry containing melamine removed from the offgas, which is located at the bottom of the quencher.

17. The melamine plant according to claim 16, wherein the quencher also comprises an inlet for an inert gas, which is located above the inlet of the solvent and below the offgas inlet.

18. The melamine plant according to claim 16, which in integrated with a urea plant, wherein the washed offgas withdrawn from the quencher are sent to the urea plant.

19. The process according to claim 9, wherein the temperature of the washed offgas is not greater than 260° C.

20. The process according to claim 10, wherein the residence time of the melamine solution or slurry in the bottom part of the quencher is not greater than 5 min.

21. The process according to claim 1, wherein the process for the synthesis of melamine from urea is of the non-catalytic high-pressure type.

22. The melamine plant according to claim 16, wherein the melamine plant is of the non-catalytic high-pressure type.

23. The melamine plant according to claim 16, wherein the liquid solvent is an aqueous solvent.

24. The melamine plant according to claim 16, wherein the outlet for withdrawing washed offgas is located on top of the quencher.

* * * * *